United States Patent
Kajii

(10) Patent No.: US 7,425,452 B2
(45) Date of Patent: Sep. 16, 2008

(54) PUMP-AND-PROBE METHOD FOR ESTIMATING STRENGTH OF FORMING PHOTOCHEMICAL OZONE AND APPARATUS THEREFOR

(75) Inventor: Yoshizumi Kajii, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 913 days.

(21) Appl. No.: 10/487,428

(22) PCT Filed: Sep. 5, 2002

(86) PCT No.: PCT/JP02/09050

§ 371 (c)(1),
(2), (4) Date: Feb. 23, 2004

(87) PCT Pub. No.: WO03/023378

PCT Pub. Date: Mar. 20, 2003

(65) Prior Publication Data
US 2004/0214340 A1    Oct. 28, 2004

(30) Foreign Application Priority Data
Sep. 6, 2001    (JP)    ............................. 2001-270301

(51) Int. Cl.
G01N 33/00    (2006.01)
G01N 21/64    (2006.01)
G01J 1/42    (2006.01)
G01J 1/58    (2006.01)

(52) U.S. Cl. .................. 436/135; 250/373; 422/83; 422/91; 436/127; 436/136; 436/172

(58) Field of Classification Search .................. 422/83, 422/91; 436/127, 135–136, 172; 250/373
See application file for complete search history.

(56) References Cited

U.S. PATENT DOCUMENTS

| 4,698,314 | A |   | 10/1987 | Tao |
| 4,849,178 | A | * | 7/1989 | Azuma ......................... 422/69 |
| 5,604,298 | A | * | 2/1997 | Dosoretz et al. ........... 783/23.2 |

FOREIGN PATENT DOCUMENTS

| JP | 7-63683 | 3/1995 |
| JP | 11-2605 | 1/1999 |
| JP | 2000-266673 | 9/2000 |

OTHER PUBLICATIONS

Wine, P. H. et al, Journal of Physical Chemistry 1985, 89, 2620-2624.*

(Continued)

Primary Examiner—Arlen Soderquist
(74) Attorney, Agent, or Firm—Westerman, Hattori, Daniels & Adrian, LLP.

(57) ABSTRACT

A method of estimating strength of forming photochemical ozone utilizing a pump and probe technique is disclosed along with an apparatus for estimating strength of forming photochemical ozone utilizing a pump and probe means whereby strength of forming photochemical ozone can be estimated without measuring a concentration of each type of various reactive hydrocarbons in order to predict strength of forming photochemical ozone from rates of their reaction with OH radicals. Atmosphere (11) is irradiated with a pumping laser light (2c) to photolyze ozone therein, thereby forming excited oxygen atoms $O(^1D)$ which are then caused to react with water vapor to form OH radicals. The OH radicals are irradiated with a probing laser light (3e) to excite electrons therein. A fluorescent light emitted when the excited electrons are relaxed to transition is measured in a time sequence. The intensity of fluorescence being proportional to the concentration of the OH radicals, the strength of forming photochemical ozone can be estimated from the change of the concentration of the OH radicals with time.

12 Claims, 2 Drawing Sheets

OTHER PUBLICATIONS

Clericetti, A. et al, SPIE 1992, 1714, 291-302.*
King, D. S. et al, Journal of Chemical Physics 1994, 100, 4200-4210.*
Silvente, E. et al, Journal of the Chemical Society, Faraday Transactions 1997, 93, 2821-2830.*
Calpini, B. et al, Analusis 1999, 27, 328-336.*
Dodd, J. A. et al, Journal of Physical Chemistry A 1999, 103, 7834-7842.*
Johnson, C. K. et al, Review of Scientific Instruments 1988, 59, 2375-2379.*
Adachi, S. et al, Optics Communications 1995, 117, 71-77.*

* cited by examiner

PUMP-AND-PROBE METHOD FOR ESTIMATING STRENGTH OF FORMING PHOTOCHEMICAL OZONE AND APPARATUS THEREFOR

This application is a national stage application of the PCT international application PCT/JP02/09050, filed on Sep. 5, 2002.

TECHNICAL FIELD

The present invention relates to a method of and apparatus for estimating a concentration or strength of forming photochemical ozone utilizing a pump and probe technique.

BACKGROUND ART

In urban areas where human activities are active, there are volatile organic compounds (VOCs) emitted notably in addition to the emissions of $NO_x$, $SO_2$ and carbon monoxide. These VOCs are emitted much more in urban areas than in the other areas. As for the VOCs, reactive hydrocarbons which react with OH radical are determinative of the strength of forming photochemical ozone in an urban area. While the reactive hydrocarbons are divergent in types, including methane, non-methane hydrocarbons (NMHCs), alcohols, and carbonyl compounds (ketones, aldehydes), the NMHCs which are highly reactive are especially important as being precursors of ozone.

The increase in the amount of emission of NMHCs as precursors of ozone in urban areas in recent years is not only recognized to accelerate the problem of air pollution in those areas but also is now pressingly to raise the important issue of adversely affecting the global atmospheric environment.

The strength or concentration of air pollutants has so far been measured using sensors which measure the individual concentrations of these NOx, $SO_2$, CO and VOCs respectively.

As for NMHCs, however, it is considered that there exist at least 200 types which are counted from an olefin to aromatic hydrocarbons, and measuring the individual concentrations of all these reactive hydrocarbons to estimate their rates of reaction with OH radicals and to estimate from their each rates the concentration or strength of ozone to be generated photo-chemically would give rise quite possibly to a large error despite the large efforts which this estimation should entail.

DISCLOSURE OF THE INVENTION

With the aforementioned prior-art problem taken into account, the present invention has for its objects to provide a method of and an apparatus for estimating strength of forming photochemical ozone or a concentration of ozone to be formed photo-chemically in an atmosphere, by a pump and probe technique whereby the strength of forming photochemical ozone can be estimated without the need to measure all of a concentration of each type of various reactive hydrocarbons in order to estimate from their rates the concentration of ozone to be generated.

In order to achieve the object mentioned above, there is provided in accordance with the present invention a method of estimating strength of forming photochemical ozone utilizing a pump and probe technique, characterized in that it comprises the steps of: irradiating atmosphere containing air pollutants with a pumping laser light to form OH radicals therefrom; irradiating such formed OH radicals with a probing laser light to cause a fluorescent light to be emitted therefrom; measuring a change of intensity of the fluorescent light with time; and determining a concentration of the air pollutants from the measured change of intensity of the fluorescent light with time.

In the method mentioned above, preferably the said pumping laser light is a pulsed laser light having its wavelength adapted to photolyze ozone in the atmosphere, thereby forming excited oxygen atoms $O(^1D)$, and the said OH radicals are formed by the reaction of the excited oxygen atoms $O(^1D)$ with water vapor. Also, the said probing laser light is preferably a pulsed laser light having its wavelength adapted to excite OH radicals.

In the method mentioned above, the said change of intensity of the fluorescent light with time may be measured by irradiating the said pumping laser light and then irradiating repetitively the said probing laser light each with a given time interval, and measuring the intensity of the fluorescent light after each time the said probing laser light is irradiated.

According to the forming photochemical ozone strength estimating method utilizing the pump and probe technique as mentioned above, the pumping laser light is used to photolyze ozone in the atmosphere and thereby to form excited oxygen atoms $O(^1D)$ which are then permitted to react with water vapor to form OH radicals. Then, irradiating such formed OH radicals with the probing laser light excites OH radicals, the excited electrons being relaxed to emit a fluorescent light whose intensity is proportional to the concentration of the OH radicals. The OH radicals are iteratively irradiated with such a probing laser light with a given time interval, and the intensity of such a fluorescent light is measured at each time after when OH radicals are irradiated with a probing laser light, whereby a change of the concentration of the OH radicals with time are found.

Since the reactive hydrocarbons in the atmosphere consume OH radicals by reacting with them, the change of the concentration of OH radicals with time increases in proportion with the concentration of the reactive hydrocarbons. It is thus possible to estimate the strength of forming photochemical ozone in the atmosphere from the measured change of the concentration of OH radicals with time, without the need to separately measure a concentration of each type of the various reactive hydrocarbons and then to predict from their concentrations the rates of their individual reactions with OH radicals in order to predict a strength of forming photochemical ozone.

The present invention also provides an apparatus for estimating strength of forming photochemical ozone utilizing a pumping and a probing means, characterized in that it comprises a pumping laser light oscillator means; a probing laser light oscillator means; a OH radical forming means; a probing laser light lead-in means; a fluorescence detection means for measuring an intensity of fluorescence; and a control means for providing the pumping laser light oscillator means, the probing laser light oscillator means and the fluorescence detection means with timing control signals whereby they are co-operated.

According to this apparatus makeup with these means operated by such timing control signals, atmosphere flowing within the radical forming means for forming OH radicals can be irradiated with a pulsed laser light to form OH radicals in the atmosphere, the OH radical in the atmosphere can be irradiated with a pulsed probing laser light introduced through the laser light lead-in means to emit a fluorescent light in the fluorescence detection means, and the intensity of the fluorescent light can be collected by a condensing mirror and condensing lenses and can then be measured by a photo detector in the fluorescence detection means.

In this apparatus, the said radical forming means preferably includes: a first and a second straight tube each connected to a side wall of said fluorescence detection means extending coaxially, and the said first straight tube having an outer end sealed hermetically with a transparent window and having an air inlet port in a region of the outer end of the said first straight tube, the said second straight tube having an outer end sealed hermetically with a transparent window and having an air out let port in a region of the outer end of the said second straight tube, whereby the atmospheric air can be led into the radical forming means, and the pumping laser light, e. g., pulsed, can be introduced into the radical forming means, passing, in the first and second straight tubes axially thereof wherein OH radicals are allowed to form. Further, the said radical forming means is preferably provided at the said air outlet port with a flow control means and a vacuum pump whereby the atmospheric air introduced into the radical forming means is allowed to flow in the first and second straight tubes at a controlled rate of flow.

According to this specific apparatus makeup, the flow control means in the air outlet port allows the atmospheric air to flow in a laminar flow optimum for the measurement and hence makes the measurement accurate. Further, the straight tubes allow the atmosphere to be sealed hermetically therein with the transparent windows provided at their opposed ends and also allow a pumping laser light to be introduced axially of the tubes so as to form OH radical reproducibly and to pass therethrough so as not to produce a stray light in the apparatus.

The said probing laser lead-in means may include: a first and a second straight tube each connected to a side wall of said fluorescence detection means extending coaxially, and each of the said first and second straight tubes having an outer end sealed hermetically with a transparent window and having a plurality of baffle plates, whereby the probing laser light, e. g., pulsed, when introduced into the first and second straight tubes may cause the OH radicals to be excited. According to this specific apparatus makeup, a pulsed probing laser light can be introduced axially of the tubes so as to excite OH radicals reproducibly and can be passed therethrough so as not to produce stray light in the apparatus. Further, the straight tubes provided with the baffle plates prevent the propagation of even a small stray light and hence make it possible to effect the measurement with an increased sensitivity.

The said fluorescence detection means may include: a condensing mirror and convex lenses means for collecting a fluorescent light generated in an area in which the first and second straight tubes of the said radical forming means and the first and second straight tubes of the said probing laser light lead-in means intersect axially, a photo detector for measuring an intensity of the collected fluorescent light, and a receptacle composed of a nontransparent material for retaining the said condensing mirror and convex lens means and the said photo detector in a sealed state. According to this specific apparatus makeup in which the condensing mirror and convex lenses means is used to collect the fluorescence emitted from a narrow area, it is possible to detect the fluorescence substantially entirely and hence to effect the measurement with an increased sensitivity and with due precision.

The said control means preferably includes a system clock means for providing a first timing signal whereby the said pumping laser light oscillator means is operated to issue a pulsed laser pumping light, a second timing signal timed on the basis of the first timing signal whereby the said probing laser light oscillator means is operated to issue a pulsed laser probing light repetitively with a given time interval, and a third timing signals whereby measurement by the said photo detector is synchronized with each pulsed laser probing light issued. According to this specific apparatus makeup, the timing can be accurately taken each of the OH radical formation, the excitation and the fluorescence detection, which assures a reproducible measurement with due sensitivity and accuracy.

The said pumping laser light oscillator means is preferably adapted to issue a pulsed laser light having a wavelength of 266 nm repetitively at a repetition rate of 1 Hz. According to this specific apparatus makeup, a pulsed pumping laser light having a wavelength of 266 nm is irradiated to atmosphere to photolyze ozone therein to form excited oxygen atoms $O(^1D)$ which are then allowed to react with water vapor to form OH radicals. The repetition cycle in which such a pulsed pumping laser light is iteratively applied to the atmosphere is as short as 1 Hz, thus reducing the measurement time period.

Also, the said probing laser light oscillator means is preferably adapted to issue a pulsed laser light having a wavelength of 281.9 nm repetitively at a repetition rate of 1 kHz. According to this specific apparatus makeup, the electron excitation of OH radicals can be effected efficiently. The repetition cycle in which such a pulsed probing laser light is iteratively applied to the atmosphere is as short as 1 kHz, permitting the electron excitation to be effected a number of times in a time interval between successive irradiations of a pulsed pumping laser light and hence the change of concentration of OH radicals with time to be measured highly accurately.

The said photo detector preferably comprises a PMT (photomultiplier tube). According to this specific apparatus makeup, high amplification factor of the PMT assures a high sensitivity of the measurement.

BRIEF DESCRIPTION OF THE DRAWINGS

The present invention will better be understood from the following detailed description and the drawings attached hereto showing certain illustrative forms of embodiment of the present invention. In this connection, it should be noted that such forms of embodiment illustrated in the accompanying drawings hereof are intended in no way to limit the present invention but to facilitate an explanation and understanding thereof. In the drawings.

BEST MODES FOR CARRYING OUT THE INVENTION

Figure 1:
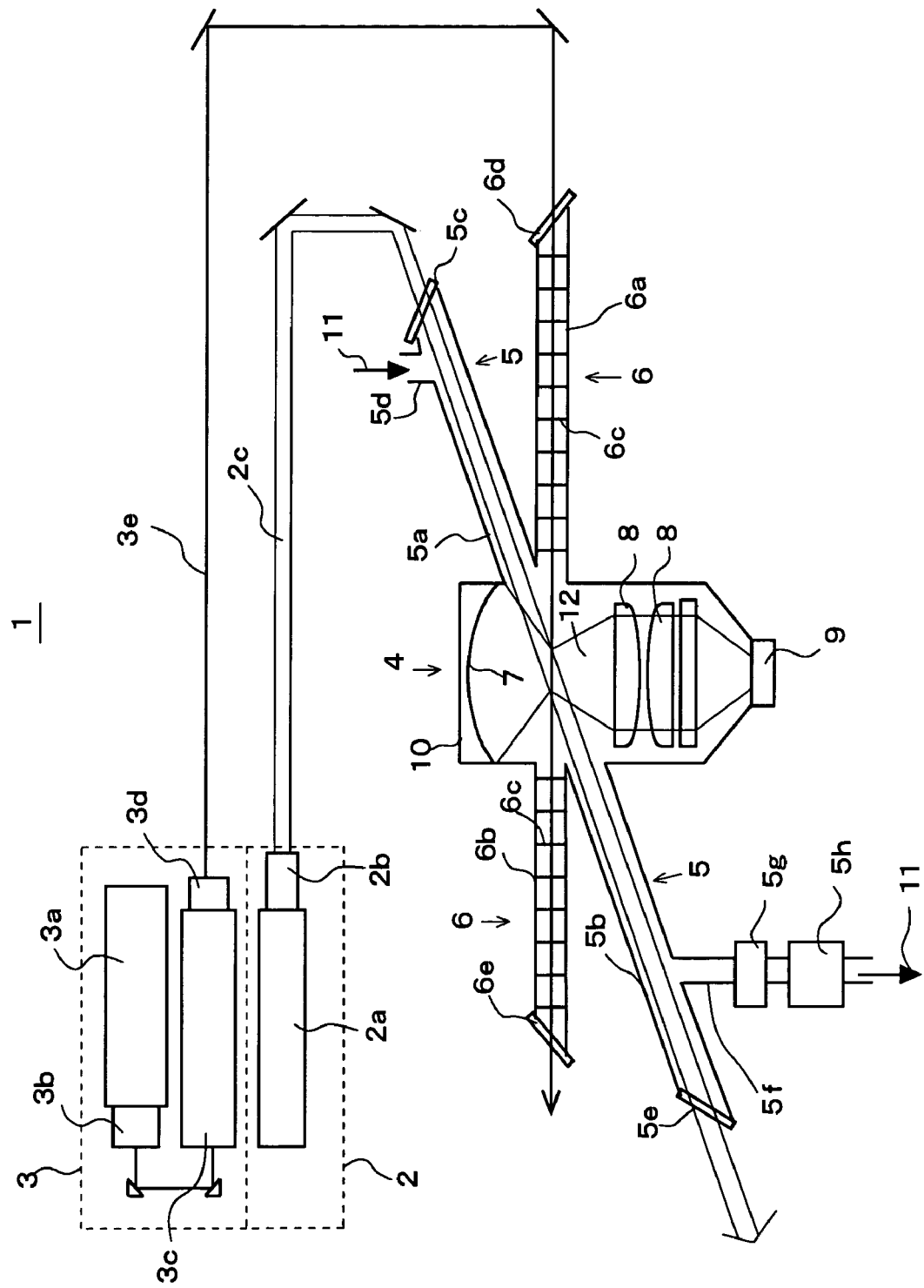
FIG. 1 shows a diagram illustrating the makeup of an apparatus for measuring the concentration of air pollutants utilizing a pump and probe technique in accordance with the present invention.

Hereinafter, the present invention will be described in detail with reference to several forms of implementation thereof illustrated in the drawing figures.

At the outset, mention is made of a mechanism in which ozone forms or is generated photo-chemically. Generating ozone (the principal component of photochemical oxidant) in the troposphere requires the presence of nitrogen oxide ($NO_x$) and carbon monoxide or a hydrocarbon (methane or a nonmethane hydrocarbon). First, ozone existing in the atmosphere absorbs the energy of a solar UV (with a wavelength shorter than 300 nm) and is photo-decomposed to form an oxygen molecule ($O_2$) and an oxygen atom in its excited state $O$ ($^1D$) in accordance with the equation:

$$O_3 + UV \rightarrow O_2 + O(^1D) \quad (1)$$

By the oxygen atom in the excited state O ($^1D$) is meant an oxygen atom with an electron therein in the excited state.

Such excited oxygen atoms thus formed are highly reactive and react with water vapor to form OH radicals in accordance with the equation:

$$O(^1D) + H_2O \rightarrow 2OH \quad (2)$$

The OH radicals are highly reactive and react with various chemical species. Since the chemical species that can react with the OH radicals which exist in a relatively clear atmosphere are limited to carbon monoxide or methane, carbon monoxide and methane here react with OH radicals in a relatively clean atmosphere (a suburban or remote area). The OH radicals react with carbon monoxide as follows:

$$OH + CO \rightarrow CO_2 + H \quad (3)$$

to form hydrogen atom (H) radicals. The hydrogen atom radicals react with oxygen molecules abundantly existing in the atmosphere as follows:

$$H + O_2 \rightarrow HO_2 \quad (4)$$

to form $HO_2$ radicals.

If OH radicals react with methane, the reactions:

$$OH + CH_4 \rightarrow H_2O + CH_3 \quad (5)$$

$$CH_3 + O_2 \rightarrow CH_3O_2 \quad (6)$$

follow to form per-oxy radicals (methyl per-oxy radical: $CH_3O_2$). These radicals may react with NO (the main component of nitrogen oxides: $NO_x$) if it exists in the atmosphere as follows:

$$CH_3O_2 + NO \rightarrow NO_2 + CH_3O \quad (7)$$

and through the reactions:

$$CH_3O + O_2 \rightarrow CH_3OO_2 \quad (8)$$

there are formed $CH_3OO_2$ radicals, which bring about monomolecular decomposition reaction:

$$CH_3OO_2 \rightarrow H_2CO + HO_2 \quad (9)$$

to form formaldehyde $H_2CO$ and $HO_2$ radicals.

In this way, ozone in the atmosphere by absorbing the ultraviolet light is decomposed to form excited oxygen atoms $O(^1D)$, which react with water vapor to form OH radicals. The OH radicals thus formed are consumed by reacting with air pollutants, e. g., carbon monoxide and/or methane.

Next, mention is made of the operations of $HO_2$ radicals formed as a result of the reaction of OH radicals with carbon monoxide or methane.

$HO_2$ radicals finally formed by the reaction of OH radicals with carbon monoxide or methane react with NO as follows:

$$HO_2 + NO \rightarrow NO_2 + OH \quad (10)$$

whereby they themselves are returned to OH radicals while NO is converted into $NO_2$, which reacts with the solar light as follows:

$$NO_2 + UV \rightarrow NO + O(^3P) \quad (11)$$

to form NO and oxygen atoms in the ground state O ($^3P$), the latter forming ozone as follows:

$$O(^3P) + O_2 \rightarrow O_3 \quad (12)$$

Thus, as long as the solar light exists, OH is converted to $HO_2$ and then returns to OH while NO is converted to $NO_2$ and then returns to NO, and the reactions expressed by equations (3) to (11) are cyclically repeated a number of times. Ozone is generated as a by-product and is accumulated. This is the atmospheric photochemical theory (theorem).

As for the urban atmosphere in which there exists an abundance of non-methane hydrocarbons (NMHCs) emitted by human activities, not only are there reactions of OH radicals with carbon monoxide and methane, but also there are their reactions with NMHCs. If the NMHC is a saturated hydrocarbon, then the reactions:

$$NMHC + OH \rightarrow H_2O + R \quad (13)$$

$$R + O_2 \rightarrow RO_2 \quad (14)$$

take place, forming alkyl peroxy radicals $RO_2$ as in the equation (8). If the NMHC is an unsaturated hydrocarbon, then the OH radicals bring about the addition reaction:

$$NMHC + OH \rightarrow ROH \quad (15)$$

to form ROH radicals, which in turn react with oxygen as follows:

$$ROH + O_2 \rightarrow ROHO_2 \quad (16)$$

whereby hydroxyl substituted $RO_2$ radicals are formed.

In either case, eventually the $HO_2$ radicals are produced as shown by the equation (9), whereafter ozone is generated following the equations (10) to (12) as with carbon monoxide or methane.

Since a NMHC and OH radicals react much faster than do methane or carbon monoxide, in the atmosphere in which both NMHCs and NOx exist abundantly it can be stated that the concentration of NMHCs is determinative of the concentration of photochemically generated or forming ozone. In the urban atmosphere there exist both NOx and NMHCs abundantly. Further, the ozone concentration varies according to the types of NMHCs.

The condition in which the primary factor that controls the ozone concentration is the hydrocarbon concentration is referred to as Hydrocarbon Limited Condition.

As for a clean atmosphere in which there is little NOx, the ozone concentration is determined by the rate of reaction from NO to $NO_2$ as shown by the equation (10). Hence, this atmospheric condition under which the generation of ozone is strongly dependent on the concentration of NOx (=NO+$NO_2$) is referred to as NOx Limited Condition.

As described above, NMHCs, which are highly reactive with OH radicals act to accelerate the photochemical formation of ozone by a series of radical chain reactions whose rate-determinative steps are the reactions between the OH radicals and the NMHCs. In other words, the concentration of NMHCs determines the life of OH radicals in the atmosphere. Thus, assuming a given amount of OH radicals, the higher the NMHC concentration, the quicker will the OH radical concentration decrease, and the lower the NMHC concentration, the slower will the OH radical concentration decrease. It follows, therefore, that measuring the change of the OH radical concentration with time allows the NMHC concentration to be estimated. The life of OH radicals is estimated to be about 1 second in the clean atmosphere but in the urban atmosphere it is estimated to be tens to hundreds of millisecond.

Mention is next made of a forming photochemical ozone strength estimating method utilizing a pump and probe technique and an apparatus for carrying out the method, in accordance with the present invention.

FIG. 1 is a diagram illustrating the makeup of an apparatus for estimating the strength of forming photochemical ozone based on a pump and probe technique in accordance with the present invention.

In FIG. 1, there is shown a forming photochemical ozone strength estimating apparatus of pump and probe type 1 which includes a pumping laser oscillator unit 2 comprising a Nd:YAG laser oscillator 2a and a $4^{th}$ harmonic generator 2b; and a probing laser oscillator unit 3 comprising a diode pumped Nd:YAG laser oscillator 3a, a $2^{nd}$ harmonic generator 3b, a variable wavelength dye laser oscillator 3c and a $2^{nd}$ harmonic generator 3d. Here, the pumping laser oscillator unit 2 is adapted to generate a pulsed pumping laser light 2c of a wavelength of 266 nm whereas the probing laser oscillator unit 3 is adapted to generate a pulsed probing laser light 3e of a wavelength of 281.9 nm.

The apparatus also includes a fluorescence detecting unit 4 having a radical forming unit 5 and a probing laser light lead-in unit 6 connected to it through its side wall regions. The radical forming unit 5 comprises a pair of straight tubes 5a and 5b of nontransparent material extending coaxially with each other and connected to the fluorescence detecting unit 4 through those side wall regions, respectively. The straight tube 5a has a transparent window 5c fastened to its outer end to hermetically seal the same and is also provided in its outer end region with an air inlet port, 5d, and the straight tube 5b has a transparent window 5e fastened to its outer end to hermetically seal the same and is also provided in its outer end region with an air outlet port 5f, which is in turn provided with a flow control unit 5g and a vacuum pump 5h.

The probing laser light lead-in unit 6 comprises a pair of straight tubes 6a and 6b of nontransparent material extending coaxially with each other and connected to the fluorescence detecting unit 4 through its side wall regions mentioned above, respectively. Each of the straight tubes 6a and 6b has a plurality of baffle plates 6c for permitting the passing light rays to propagate only axially thereof and also has a transparent window 6d, 6e fastened to its outer end to hermetically seal the same.

The radical forming unit 5 and the probing laser light lead-in unit 6 are connected to the side walls of the fluorescence detecting unit 4 transversely to each other so that their axes intersect at a point in its inside.

The fluorescence detecting unit 4 is designed to collect fluorescence generated in a region where the axis of the radical forming unit 5 and the axis of the probing laser light lead-in unit 6 intersect and to this intersect region is provided with a condensing mirror 7, convex lenses 8 and a photo detector 9 for measuring the intensity of the condensed light, and a receptacle 10 made of nontransparent material for retaining therein the condensing mirror 7, the convex lenses 8 and the photo detector 9 in a sealed state.

Figure 2:
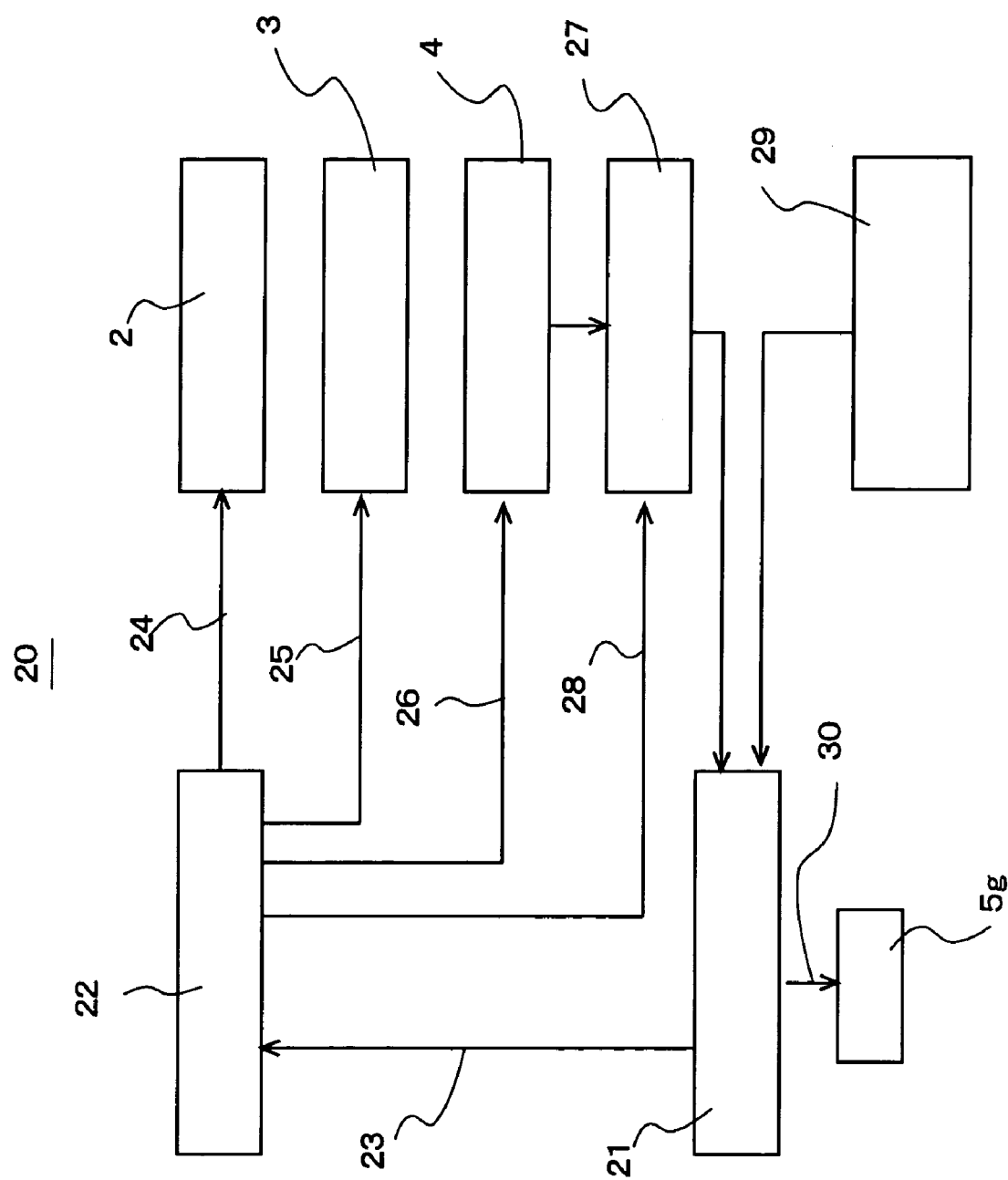
FIG. 2 represents a diagram illustrating a control system for the apparatus for measuring the concentration of air pollutants utilizing the pump and probe technique in accordance with the present invention

The forming photochemical ozone strength estimating apparatus based on the pump and probe technique operates controlled by a control system 20 as shown in FIG. 2. The control system 20 includes a processing and integrated control unit 21 adapted to furnish a system clock generator 22 with a control signal 23 indicating a start of measurement. The system clock generator 22 upon receipt of the control signal 23 is adapted to generate system clocks and count the system clocks to generate a control signal each time each of preselected counts is reached in an order mentioned below.

First, the pumping laser oscillator unit 2 is furnished with a control signal 24 to issue a pumping laser light pulse 2c (FIG. 1). Then, the probing laser oscillator unit 3 is furnished with a control signal 25 to issue a probing laser light pulse 3e. The fluorescence detecting unit 4 is furnished with a control signal 26 to measure a fluorescence intensity in the form of an analog signal for a given time period. Then, a detection signal A/D conversion unit 27 is furnished with a control signal 28 to convert the analog signal representing the fluorescent intensity measured by the fluorescence detecting unit 4 into a digital signal, which is delivered to the processing and integrated control unit 21.

A cycle is set of these steps starting with the step of furnishing the probing laser oscillator unit 3 with a control signal 25 and ending with the step of furnishing the detection signal A/D conversion unit 27 with a control signal 28 and this cycle is repeated a given number of times. After the cycle is so repeated, the pumping laser oscillator unit 2 is again furnished with a control signal 24 whereafter the cycle is again repeated. Thus, for example, the pumping laser oscillator unit 2 is repetitively furnished with control signal at a cycle of 1 Hz and the probing laser oscillator unit 3 is repetitively furnished with a control signal 25 at a cycle of 1 kHz.

The processing and integrated control unit 21 is responsive to a signal from a laser fluctuation compensation system 29 to furnish each of the pumping laser oscillator unit 2 and the probing laser oscillator unit 3 with a sequential control signal to maintain the laser light intensity therefrom at a given value while furnishing the flow control unit 5g with a control signal 30 to maintain the air flow in the radical forming unit 5 at a given value.

Operating the forming photochemical ozone strength estimating apparatus 1 utilizing the pump and probe technique in accordance with the present invention allows the atmosphere 11 introduced through the air inlet port 5d to flow through the radical forming unit 5 passage in a laminar flow whose flow velocity is controlled by the vacuum pump 5h and the flow control unit 5g at a speed of flow optimum for measurement. The pumping laser light pulse 2c is introduced through the transparent window 5c of the radical forming unit 5 to pass along its axis, and the atmosphere 11 in the radical forming unit 5 upon absorbing the energy of the pulsed pumping laser light 2c gives rise to oxygen atoms in their excited state O ($^1$D), which then react with water vapor in the atmosphere, thus forming OH radicals. The OH radicals react with air pollutants in the atmosphere, i. e., reactive hydrocarbons such as NMHCs and methane, and their concentration then gradually decreases. The probing laser light pulse 3e is introduced through the transparent window 6d of the probing laser light lead-in unit 6 to pass along its axis. The OH radicals in the atmosphere 11 in an area in the fluorescence detection unit 4 where the radical forming unit 5 and the probing laser lead-in unit 6 intersect absorb the pulsed probing laser light 3e so that their electrons are excited, and then when transitioned to their ground state emit a fluorescent light 12.

The fluorescent light 12 is collected by the condensing mirror and lenses 7 and 8, and its intensity is measured by the PMT 9. After the pulsed pumping laser light 2c is pumped to irradiate in the atmosphere therewith, the pulsed probing laser light 3e is irradiated the atmosphere therewith a plurality of times and each time the probing irradiation occurs the fluorescent intensity is measured to determine its change with time. Since the fluorescent intensity is proportional to the concentration of the OH radicals, the life of the OH radicals or the change of the OH radical concentration with time can be found from determining the change of the fluorescent intensity with time.

As mentioned above in connection with the equations (13) to (16), OH radicals are consumed by their reaction with NMHCs. Thus, the more larger concentration of NMHCs in the atmosphere, the faster change of the concentration of OH radicals with time, and the smaller concentrations of NMHCs in the atmosphere, the slower change of the concentration of OH radicals with time.

Also, since $HO_2$ radicals produced by the reaction of NMHCs with OH radicals cause photochemical ozone to form as mentioned hereinbefore in connection with the equations (10) to (12), it is possible to estimate the concentration or strength of the forming photochemical ozone from the magnitude of the change of the concentration or strength of the OH radicals with time. To wit, for the atmosphere in which there exist an abundance of NMHCs and also an abundance of NOx and where photochemical ozone forms under the hydrocarbon limited conditions as mentioned above, it is possible to estimate the strength of the forming photochemical ozone from the magnitude of the change of the strength of OH radicals with time.

In the method of the present invention, the rate-determining reactions in the photochemical ozone forming reactions in an atmosphere are actually excited in this apparatus and the quantity corresponding to the rate of the reaction is measured. It is therefore possible to estimate easily and precisely the strength of the forming photochemical ozone actually to be formed in the atmosphere, regardless of the types of air pollutants. More precisely mentioned, for example, given a similarity coefficient between the energy of a pulsed pumping irradiating laser light to the solar energy in an actual environment, it is possible by using the coefficient to estimate the strength of actually forming photochemical ozone from a change of the strength of OH radicals with time as determined by the method and apparatus of the present invention.

INDUSTRIAL APPLICABILITY

It will be appreciated from the foregoing description that according to the present invention it is possible to estimate easily and accurately the forming strength of photochemical ozone without measuring the strength or concentration of each individual type of reactive hydrocarbons in order to predict the strength of forming photochemical ozone from the rates of their reaction with OH radicals. There is thus provided in accordance with the present invention a method that is vital and essential to performing the measurement of air pollution in an urban area, and further of air pollution in the global atmosphere with ease and precision, as well as an apparatus for carrying out the method.

What is claimed is:

1. A method of estimating strength of forming photochemical ozone utilizing a pump and probe technique, characterized in that it comprises the steps of: irradiating atmosphere containing pollutants with a pumping laser light to form OH radicals therefrom;
    irradiating such formed OH radicals with a probing laser light to cause a fluorescent light to be emitted therefrom;
    measuring a change of intensity of the fluorescent light with time; and
    determining a concentration of the air pollutants from the measured change of intensity of the fluorescent light with time,
    wherein the pumping laser light has a wavelength of 266 nm repetitively at a repetition rate of 1 Hz, and the probing laser light has a wavelength of 281.9 nm repetitively at a repetition rate of 1 kHz.

2. The method of estimating strength of forming photochemical ozone utilizing a pump and probe technique as set forth in claim 1, characterized in that said pumping laser light is a pulsed laser light having its wavelength adapted to photolyze ozone in the atmosphere, thereby forming excited oxygen atoms $O(^1D)$.

3. The method of estimating strength of forming photochemical ozone utilizing a pump and probe technique as set forth in claim 1, characterized in that said OH radicals are formed by the reaction of the excited oxygen atoms $O(^1D)$ with water vapor.

4. The method of estimating strength of forming photochemical ozone utilizing a pump and probe technique as set forth in claim 1, characterized in that said probing laser light is a pulsed laser light having its wavelength adapted to excite electrons in the OH radicals.

5. The method of estimating strength of forming photochemical ozone utilizing a pump and probe technique as set forth in claim 1, characterized in that said change of intensity of the fluorescent light with time is measured by irradiating said pumping laser light and then irradiating said probing laser light repetitively each with a given time interval, and measuring the intensity of the fluorescent light after each time said probing laser light is irradiated.

6. An apparatus for estimating strength of forming photochemical ozone utilizing a pump and a probe means, characterized in that it comprises:
    a pumping laser light oscillator means;
    a probing laser light oscillator means;
    an OH radical forming means;
    a probing laser light lead-in means;
    a fluorescence detection means for measuring an intensity of fluorescence; and
    a control means for providing said pumping laser light oscillator means, said probing laser light oscillator means and said fluorescence detection means with timing control signals whereby they are co-operated,
    wherein the pumping laser light oscillator means is adapted to issue a pulsed laser light having a wavelength of 266 nm repetitively at a repetition rate of 1 Hz, and the probing laser light oscillator means is adapted to issue a pulsed laser light having a wavelength of 281.9 nm repetitively at a repetition rate of 1 kHz.

7. The apparatus for estimating strength of forming photochemical ozone utilizing a pump and a probe means as set forth in claim 6, characterized in that said radical forming means includes:
    a first and a second straight tube extending coaxially and each connected to a side wall of said fluorescence detection means, said first straight tube having an outer end sealed hermetically with a transparent window and having an air inlet port in a region of the outer end of said first straight tube, said second straight tube having an outer end sealed hermetically with a transparent window and having an air out let port in a region of the outer end of said second straight tube,
    whereby the atmosphere can be led into the radical forming means, flowing, and the pumping laser light, e. g., pulsed, can be introduced into the radical forming means, passing in the first and second straight tubes axially thereof whereby the OH radicals are allowed to form therein.

8. The apparatus for estimating strength of forming photochemical ozone utilizing a pump and a probe means as set forth in claim 6, characterized in that said radical forming means is provided at said air outlet port with a flow control means and a vacuum pump whereby the atmosphere introduced into the radical forming means is allowed to flow in the first and second straight tubes at a controlled rate of flow.

9. The apparatus for estimating strength of forming photochemical ozone utilizing a pump and a probe means as set forth in claim 6, characterized in that said probing laser lead-in means includes:

a first and a second straight tube extending coaxially and each connected to a side wall of said fluorescence detection means, each of said first and second straight tubes having an outer end sealed hermetically with a transparent window and having a plurality of baffle plates, whereby the probing laser light, e. g., pulsed, when introduced into the first and second straight tubes may cause electrons in the OH radicals to be excited.

10. The apparatus for estimating strength of forming photochemical ozone utilizing a pump and a probe means as set forth in claim 6, characterized in that said fluorescence detection means includes:

a condensing mirror and convex lens means for collecting a fluorescent light generated in an area in which the first and second straight tubes of said radical forming means and the first and second straight tubes of said probing laser light lead-in means intersect axially, a photo detector for measuring an intensity of the collected fluorescent light, and a receptacle composed of a nontransparent material for retaining said condensing mirror and convex lens means and said photo detector in a sealed state.

11. The apparatus for estimating strength of forming photochemical ozone utilizing a pump and a probe means as set forth in claim 6, characterized in that said control means includes a system clock means for providing a first timing signal whereby said pumping laser light oscillator means is operated to issue a pulsed pumping laser light, a second timing signal timed on the basis of the first timing signal whereby said probing laser light oscillator means is operated to issue a pulsed laser probing light repetitively with a given time interval, and a third timing signal whereby measurement by said photo detector is synchronized with each pulsed probing laser light issued.

12. The apparatus for estimating strength of forming photochemical ozone utilizing a pump and a probe means as set forth in claim 6, characterized in that said photo detector comprises a PMT (photomultiplier tube).

\* \* \* \* \*